United States Patent
Steinberg et al.

(10) Patent No.: US 11,633,122 B2
(45) Date of Patent: Apr. 25, 2023

(54) PORTABLE SUB-THZ AND THZ RADAR SYSTEM FOR REMOTE PHYSIOLOGICAL PARAMETERS DETECTION AND METHOD WITH HARMONIC AND FUNDAMENTAL COMPONENTS

(71) Applicant: NETEERA TECHNOLOGIES LTD., Jerusalem (IL)

(72) Inventors: Yochanan Steinberg, Jerusalem (IL); Yizhaq Litman, New York, NY (US)

(73) Assignee: NETEERA TECHNOLOGIES LTD., Jerusalem (IL)

( * ) Notice: Subject to any disclaimer, the term of this patent is extended or adjusted under 35 U.S.C. 154(b) by 166 days.

(21) Appl. No.: 17/257,783

(22) PCT Filed: Feb. 14, 2019

(86) PCT No.: PCT/IL2019/050180
§ 371 (c)(1),
(2) Date: Jan. 4, 2021

(87) PCT Pub. No.: WO2020/012455
PCT Pub. Date: Jan. 16, 2020

(65) Prior Publication Data
US 2022/0079464 A1    Mar. 17, 2022

Related U.S. Application Data

(60) Provisional application No. 62/787,765, filed on Jan. 3, 2019, provisional application No. 62/703,452, filed (Continued)

(51) Int. Cl.
*A61B 5/0507*    (2021.01)
*A61B 5/00*    (2006.01)
(Continued)

(52) U.S. Cl.
CPC .......... *A61B 5/0507* (2013.01); *A61B 5/0002* (2013.01); *A61B 5/0033* (2013.01); *A61B 5/024* (2013.01); *A61B 5/165* (2013.01)

(58) Field of Classification Search
CPC ... A61B 5/0507; A61B 5/0205; A61B 5/0002; A61B 5/0033; A61B 5/024; A61B 5/165;
(Continued)

(56) References Cited

U.S. PATENT DOCUMENTS 6,122,573 A    9/2000 Higashi et al.
7,272,431 B2   9/2007 Mcgrath
(Continued)

FOREIGN PATENT DOCUMENTS

CN    106037644 A    10/2016
DE    19626556 A1    1/1998

OTHER PUBLICATIONS

Sasan Bakhtiari teaches Compact Millimeter-Wave Sensor for Remote Monitoring of Vital Signs. (Year: 2012).*
(Continued)

*Primary Examiner* — Serkan Akar
(74) *Attorney, Agent, or Firm* — Dorsey & Whitney LLP

(57) ABSTRACT

The present invention provides a method and a portable non-invasive sub-THz and THz (THz) radar system for remotely detecting physiological parameters of a subject, comprising: one or more transmission means for transmitting THz signals to a subject predefined tissue; one or more reception means for receiving a THz signal of the subject, the THz signals being a reflection of the THz signal from subject tissue thereby, receiving at least one physiological parameter change; and microprocessor means coupled and configured to communicate with the transmitter means and/ or the reception means for receiving and processing the reflected signals. The microprocessor comprising instruc-
(Continued)

tions of pre-treatment and folding the reflected signals; filtering and decimating selected portions of the folded signals and removing folded segments; decomposing of the decimated signal s into sub-component signals: identifying and removing sub-component signals due to random motions; locating quasi-periodic signal information from the remaining sub-component signals thereby, determining at least one physiological parameter of the subject based upon the quasi-periodic signal information components.

19 Claims, 13 Drawing Sheets

Related U.S. Application Data on Jul. 26, 2018, provisional application No. 62/695,205, filed on Jul. 9, 2018.

(51) Int. Cl.
*A61B 5/024* (2006.01)
*A61B 5/16* (2006.01)

(58) Field of Classification Search
CPC ....... A61B 5/1102; A61B 5/1135; A61B 5/18; A61B 2503/22; A61B 5/6893; A61B 5/746; G08B 21/06; G01S 7/354; G01S 7/358; G01S 13/34
See application file for complete search history.

(56) References Cited

U.S. PATENT DOCUMENTS

| | | |
|---|---|---|
| 7,811,234 B2 | 10/2010 | Mcgrath |
| 8,428,696 B2 | 4/2013 | Foo |
| 8,814,805 B2 | 8/2014 | Lin et al. |
| 9,057,785 B1 | 6/2015 | Lee |
| 9,164,168 B2 | 10/2015 | Petkie |
| 9,200,945 B2 | 12/2015 | Lin et al. |
| 9,477,812 B2 | 10/2016 | Lin et al. |
| 9,520,051 B1 | 12/2016 | Zack et al. |
| 9,532,735 B2 | 1/2017 | Sana et al. |
| 9,568,595 B2 | 2/2017 | Zack et al. |
| 9,649,033 B2 | 5/2017 | Ziganshin et al. |
| 2010/0241009 A1 | 9/2010 | Petkie |
| 2010/0241010 A1 | 9/2010 | Lin et al. |
| 2013/0245437 A1 | 9/2013 | Gamble et al. |
| 2015/0018676 A1 | 1/2015 | Barak |
| 2015/0181840 A1 | 7/2015 | Tupin et al. |
| 2015/0241555 A1 | 8/2015 | Lin et al. |
| 2016/0228010 A1 | 8/2016 | Kim et al. |
| 2016/0338599 A1 | 11/2016 | Debusschere et al. |
| 2017/0119318 A1 | 5/2017 | Shay et al. |
| 2018/0106897 A1 | 4/2018 | Shouldice et al. |
| 2018/0256082 A1 | 9/2018 | Steinberg et al. |
| 2020/0205726 A1* | 7/2020 | Lee .................... G01S 13/87 |

OTHER PUBLICATIONS

International Search Report and Written Opinion from International Application No. PCT/IL2019/050180 dated Jun. 19, 2019.
Non-Final Office Action for U.S. Appl. No. 15/861,721 dated Sep. 23, 2020.
U.S. Appl. No. 15/636,667, filed Jun. 29, 2017.
U.S. Appl. No. 62/470,256, filed Mar. 12, 2017.
U.S. Appl. No. 62/470,259, filed Mar. 12, 2017.
U.S. Appl. No. 62/695,205, filed Jul. 9, 2018.
U.S. Appl. No. 62/703,452, filed Jul. 26, 2018.
U.S. Appl. No. 62/787,765, filed Jan. 3, 2019.
Mikhelson, et al., "Remote Sensing of Heart Rate and Patterns of Respiration on a Stationary Subject Using 94-GHz Millimeter-Wave Interferometry", IEEE Transactions on Biomedical Engineering, IEEE Service Center, Piscataway, NJ, USA, vol. 58, No. 6, Jun. 1, 2011, pp. 1671-1677.
Petkie, et al., "Remote Respiration and Heart Rate Monitoring With Millimeter-Wave/Terahertz Radars", Proceedings of the SPIE—Smart Structures and Materials 2005: Smart Electronics, Mems, Biomems, and Nanotechnologyproceedings of the SPIE, vol. 7117, Oct. 2, 2008, p. 711701.
Examination Report No. 1 for Australian Application No. 2019301299 dated Sep. 7, 2021.
Notice of Acceptance for Australian Application No. 2019301299 dated Nov. 24, 2021.
"Quasiperiodic Function", https://en.wikipedia.org/wiki/Quasiperiodic_function, 2022, 2 pages.
Trivino, et al., "Comprehensible Model of a Quasi-Periodic Signal", European Centre for Soft Computing Internal Report, Dec. 2009, pp. 1-10.

* cited by examiner

PORTABLE SUB-THZ AND THZ RADAR SYSTEM FOR REMOTE PHYSIOLOGICAL PARAMETERS DETECTION AND METHOD WITH HARMONIC AND FUNDAMENTAL COMPONENTS

FIELD OF INVENTION

The present invention pertains to the sub-THz and THz radar system and method. More particularly, the present invention pertains to a sub-THz and THz radar system and method for physiological parameters detection.

BACKGROUND OF THE INVENTION

With the proliferation of computing devices from automobiles to home and industrial appliances, users increasingly desire seamless and intuitive ways to detect a variety of parameters. Resulting from this need, detection means have proliferated for these computing devices.

These conventional detection devices are expensive, in some cases massive, require contact, sensitive to motion or friction and fail to provide non-contact seamless and efficient detection desired by users.

Therefore, there is still a long felt unmet need for a portable device and system having high detection efficiency pertaining to a variety of applications and requirements for health characteristic and parameters detection.

SUMMARY OF THE INVENTION

It is an object of the present invention to disclose a method of remotely detecting at least one physiological parameter of at least one subject in a space, comprising steps of: providing a portable non-invasive sub-THz and THz radar system for remotely detecting physiological parameters of a subject, comprising:
  one or more transmission means for transmitting sub-THz and THz (THz) signals to a subject tissue;
  one or more reception means for receiving the THz signals of the subject, the THz signals being a reflection of the THz signal from the subject tissue; and,
  microprocessor means communicating with transmission means and/or reception means for receiving and processing the reflected signals;
  pre-treatment and folding the reflected signals by the microprocessor means, filtering and decimating selected portions of the folded signals and removing folded segments;
  decomposing of the decimated signals into sub-component signals;
  identifying and removing sub-component signals due to random motions;
  locating quasi-periodic signal information from the remaining sub-component signals thereby, determining at least one physiological parameter of the subject based upon the quasi-periodic signal information components.

It is another object of the present invention to disclose the method as mentioned in any of the above, wherein additionally comprising steps of generating one or more physiological parameter profile characterized by average heart rate vs. time, heartbeat to heartbeat interval, variation in average heart rate, variation in heartbeat interval, temporal or spectral change in heart rate variations, respiration intervals, variations in respiration rates, and/or respiration amplitude.

It is another object of the present invention to disclose the method as mentioned in any of the above, wherein additionally comprising collecting the physiological parameters in real time by user demand, system offline/online activation or predefined instructions.

It is another object of the present invention to disclose the method as mentioned in any of the above, wherein additionally comprising transmitting an output to a user selected from the group consisting of: an automatic alert, an activation instruction of an electronic device, an electronic message, a flag and a combination thereof.

It is another object of the present invention to disclose the method as mentioned in any of the above, wherein additionally comprising associating the physiological parameter information with a cloud-based system.

It is another object of the present invention to disclose the method as mentioned in any of the above, wherein further comprising:
  (a) storing the physiological parameters signal information;
  (b) interpretation of real time received signals compared to stored subject signal information;
  (c) indicating subject health status selected from the group consisting of fatigue, sleep, stress, anxiety, physiological crisis, comfort level and a combination thereof; and
  (d) exporting an alert, an electronic message, a flag or an activation instruction of electronic circuit or device, associated with the health status It is another object of the present invention to disclose the method as mentioned in any of the above, wherein selecting the physiological parameters from the group consisting of: heart rate, heart rate intervals, heart rate variabilities, respiratory rate, respiratory rate variability, respiration amplitude, respiration amplitude variability, blood pressure, body temperature, body fluids, vocal cord, eye movement, body movement, motion status and a combination thereof.

It is another object of the present invention to disclose the method as mentioned in any of the above, wherein additionally comprising wireless communication means for communicating with a subject, a user, a medical center, a caregiver, an electronic device, one or more vehicle and any combination thereof.

It is another object of the present invention to disclose the method as mentioned in any of the above, wherein the physiological parameters are collectable in real time by user demand, system offline/online activation or predefined instructions.

It is another object of the present invention to disclose the method as mentioned in any of the above, wherein further comprising a subject classification for identifying and ranking subject's received physiological parameter signals according to at least one identification data selected from the group consisting of: subject's age, gender, race, physiological condition, mental condition, health condition, medical health history and a combination thereof.

It is another object of the present invention to disclose the method as mentioned in any of the above, wherein additionally comprising simultaneously monitoring and/or identifying multiple subjects in a predefined location.

It is another object of the present invention to disclose the method as mentioned in any of the above, wherein, additionally comprising providing sensory data fusion via at least one sensor such as a camera or any thermographic camera.

It is another object of the present invention to disclose a portable non-invasive sub-THz and THz (THz) radar system for remotely detecting physiological parameters of a subject, comprising:

one or more transmission means for transmitting THz signals to a subject predefined tissue; one or more reception means for receiving a THz signal of the subject, the THz signals being a reflection of the THz signal from subject tissue thereby, receiving at least one physiological parameter change; and, microprocessor means coupled and configured to communicate with the transmitter means and/or the reception means for receiving and processing the reflected signals;

wherein the microprocessor comprising instructions of pre-treatment and folding the reflected signals;

filtering and decimating selected portions of the folded signals and removing folded segments;

decomposing of the decimated signals into sub-component signals;

identifying and removing sub-component signals due to random motions;

locating quasi-periodic signal information from the remaining sub-component signals thereby, determining at least one physiological parameter of the subject based upon the quasi-periodic signal information components.

It is another object of the present invention to disclose the system as mentioned in any of the above, wherein the reception means comprise at least one antenna receiver.

It is another object of the present invention to disclose the system as mentioned in any of the above, wherein the transmission means comprise at least one antenna transmitter.

It is another object of the present invention to disclose the system as mentioned in any of the above, wherein the system is placed in a housing selected from the group consisting of: a smartwatch, a microphone, a helmet, headphones or any Head-mounted displays, a clothing article, a garment, a bracelet or any wrist device, neckless, a finger ring, glasses, goggles, a patch, an electronic device and any other platform.

It is another object of the present invention to disclose the system as mentioned in any of the above, wherein additionally comprising at least one additional sensor source for sensory data fusion.

It is another object of the present invention to disclose the system as mentioned in any of the above, wherein the physiological parameters are collectable in real time by user demand, system offline/online activation or predefined instructions.

It is another object of the present invention to disclose the system as mentioned in any of the above, wherein the microprocessor means configured to isolate un-predefined motion streams of signal data into fundamental components to extract the signal of the predefined physiological parameter.

It is another object of the present invention to disclose the system as mentioned in any of the above, wherein additionally comprising transmitting an output to a user selected from the group consisting of: an automatic alert, electronic message, a flag, activation instruction of electronic device and a combination thereof.

It is another object of the present invention to disclose the system as mentioned in any of the above, wherein the microprocessor is configured to associate the physiological parameter information with a cloud-based system.

It is another object of the present invention to disclose the system as mentioned in any of the above, wherein the microprocessor means configured to process the signals to provide a respiratory profile pattern and/or a heart rate profile pattern of the subject.

It is another object of the present invention to disclose the system as mentioned in any of the above, wherein selecting the physiological parameters from the group consisting of: heart rate, heart rate intervals, heart rate variabilities, respiratory rate, respiratory rate variability, respiration amplitude, respiration amplitude variability, blood pressure, body temperature, body fluids, vocal cord, eye movement, body movement, motion status and a combination thereof.

It is another object of the present invention to disclose the system as mentioned in any of the above, wherein additionally comprising wireless communication means for communicating with a subject, a user, a medical center, an electronic device, one or more vehicle, a caregiver and any combination thereof.

It is another object of the present invention to disclose the system as mentioned in any of the above, wherein the physiological parameters are collectable in real time by user demand, system offline/online activation or predefined instructions.

It is another object of the present invention to disclose the system as mentioned in any of the above, wherein further comprising a subject classification for identifying subject's received physiological parameter signals according to at least one identification data selected from the group consisting of: subject's age, gender, race, physiological condition, mental condition, health condition, medical health history and a combination thereof.

It is another object of the present invention to disclose the system as mentioned in any of the above, wherein additionally comprising simultaneously monitoring and/or identifying multiple subjects in a predefined location.

It is another object of the present invention to disclose the system as mentioned in any of the above, wherein additionally comprising an indication regarding subject health status selected from the group consisting of: fatigue, sleep, stress, anxiety, physiological crisis, comfort level and a combination thereof.

It is another object of the present invention to disclose the system as mentioned in any of the above, wherein additionally comprising exporting an alert, an electronic message, a flag or an activation instruction of electronic circuit or device, associated with the health status.

It is an object of the present invention to disclose a portable wearable device for remotely detecting physiological parameters of a subject, comprising:

a sub-THz and THz (THz) radar system for remotely detecting physiological parameters of a subject, comprising:

one or more transmission means for transmitting THz signals to a subject predefined tissue;

one or more reception means for receiving a THz signal of the subject, the THz signals being a reflection of the THz signal from subject tissue thereby, receiving at least one physiological parameter change; and, microprocessor means coupled and configured to communicate with the transmitter means and/or the reception means for receiving and processing the reflected signals;

wherein the microprocessor comprising instructions of pre-treatment and folding the reflected signals;

filtering and decimating selected portions of the folded signals and removing folded segments;

decomposing of the decimated signals into sub-component signals;

identifying and removing sub-component signals due to random motions;

locating quasi-periodic signal information from the remaining sub-component signals thereby, determining at least one physiological parameter of the subject based upon the quasi-periodic signal information components.

BRIEF DESCRIPTION OF THE FIGURES

In order to better understand the invention and its implementation in practice, a plurality of embodiments will now be described, by way of non-limiting example only, with reference to the accompanying drawings, wherein.

DETAILED DESCRIPTION OF THE PRESENT INVENTION

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a system and a method for Sub-THz and THz detection of physiological parameters using circuit means.

The present invention provides device, system, and method of remote monitoring of subject physiological parameters and/or health conditions using a Sub-THz and THz radio-frequency electromagnetic field.

The present invention further provides a system comprising a Sub-THz and THz based radar system configured to detect and monitor in real time at least one physiological parameter of at least one subject such as an adult, an infant, a toddler, a baby, a child, an elderly subject, an occupant, and/or an animal. The detection may be within a distance, a space, environment, posture, gesture, location, direction or/and any position. The predefined space may be a vehicle, an autonomous vehicle, a public and private transportation, a medical and/or health institute, home environment, work environment, publicly and privately accessible domains/businesses and any other defined location.

Figure 1:
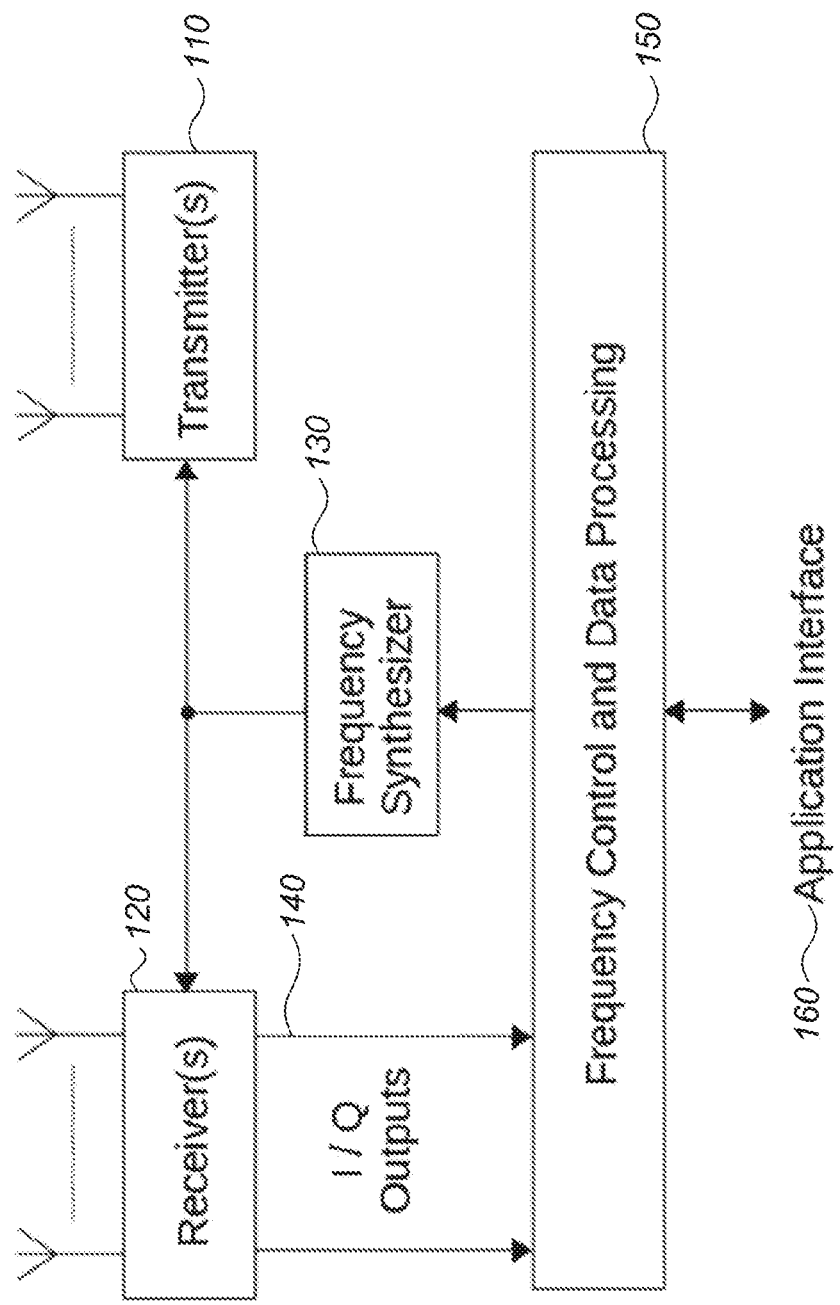
FIG. 1 presents an example of a schema of the Sub-THz and THz radar system according to an exemplary embodiment of the disclosure.

Reference is now made to FIG. 1 which presents a Tx-Rx FMCW or CW Sub-THz and THz based radar system as a remote portable non-contact detection system. The system is comprising: one or more transmission means for transmitting sub-THz and THz signals to a subject body or tissue and one or more reception means for receiving the sub-THz and THz signal of the subject. The received sub-THz and THz signals being a reflection of the sub-THz and THz signal from subject thereby, containing information about at least one physiological parameter associated with the subject.

As illustrated in FIG. 1 the THz radar system may comprise at least one transmitter (Tx) 110 and at least one receiver 120 coupled with integrated antennas. The FMCW radar transmits a signal with periodic frequency modulation. In order to get accurate frequency and frequency modulation the transmitted signal may be generated by a frequency synthesizer 130. The received signals are convened to intermediate frequency (IF) domain to obtain in-phase and quadrature-phase (IQ) signals 140. Depending on the application the IF may be nonzero (superheterodyne receiver) or zero (direct conversion receiver).

In other embodiments of the present invention, the system may comprise a heterodyne receiver such that filtering conversion to baseband and demodulation may be performed in the analog IF or after sampling and A/D conversion of the digital domain. The system may further comprise frequency control and any data processing means 150.

In other embodiments of the present invention, the radar system may be controlled, and the received data may be obtained via an application interface 160.

In other embodiments of the present invention, the radar system may be characterized by a monolithic microwave integrated circuit (MMIC) chip, in which an active circuit comprising an oscillator and a mixer is monolithically formed with at least one antenna or plurality of antennas on a semiconductor substrate. Furthermore, the MMIC may be sealed with a package such as a resin package. Furthermore, the system antenna, the active circuit and/or the packaging may be at least partially monolithically formed.

In another embodiment a method for multiplying the capacity of a radio link may be used when using multiple transmit and receive antennas (i.e. MIMO) to exploit multipath propagation.

In another embodiment of the present invention, a dielectric lens may be formed on the package to attain a desired beamwidth. Furthermore, the lens and the package may integrally be formed using any known in-mold technology In other embodiments of the present invention, the system may further comprise an integrated PLL-based fractional frequency synthesizer. The frequency synthesizer on a circuit chip may comprise a fractional divider, a modulator for modifying the divisor of the fractional divider and a ramp generator configured to generate a ramp for sweeping the frequency of the frequency synthesizer. The frequency synthesizer may further comprise an interface circuit configured to control the ramp generator.

In other embodiment, the PLL means is configured to provide an accurate Tx frequency control. The PLL may be operated with external VCO and generate the frequency modulation waveform for a FMCW radar.

The term 'Terahertz' or 'THz' refers herein to Terahertz and Sub-Terahertz radiation—also known as sub-millimeter and millimeter wave radiation, terahertz waves, tremendously high frequency (THF), or THz—consists of electromagnetic waves within the ITU-designated band of frequencies from 0.03 to 3 terahertz (THz; 1 THz=$10^{12}$ Hz). Wavelengths of radiation in the terahertz band correspondingly range from 10 mm to 0.1 mm (or 100 μm). The term 'Physiologlcal Parameters' herein refers to any physiological indicator, vital sign, cardiac or pulmonary metrics, medical condition, health indicator or health characteristic such as heart rate, (HR), respiratory rate, (RR), heart rate variability, (HRV), respiration amplitude, (RA), respiration amplitude variability, respiration rate variability, (RRV), ballistocardiogram(BCG), BCG amplitude variability, pulse wave velocity, (PWV), blood pressure (i.e. MAP, systolic and diastolic), vascular resistance, body temperature, pulse pressure variability, stroke volume and variability, body fluid (such as sweat, saliva and/or tears), body movement derived from vocal cord vibration, eye movement, body or skin movement due to speech, motion classification such as speaking or singing, change in voice sound, micro skin motions and body motion (such as seizures, tremors, shaking, trembling and/or vibrating).

In other embodiments of the present invention, vital signs, such as HR, RR, HRV, RA, RRV, and BCG may be processed from the received and/or recorded signals. Analysis of the relevant spatial (i.e. amplitude) and temporal (i.e. time dependent) characteristics of the signal data enables temporal and/or spectral separation between respiration and heart rate related signal components.

The term 'Microprocessor' or Microprocessor Means' refers herein to at least one computer processor that incorporates the functions of a central processing unit (CPU) on a single integrated circuit (IC), or several integrated circuits. The microprocessor is configured to receive input and provide the relevant output. The microprocessor is further configured to perform analysis, calculation, data processing, automated reasoning, storing and/or processing the received sub-THz and THz signals and detect at least one physiological parameter.

The microprocessor may further detect, compare and provide interpretation of the received signal indicating of a change in subject's health condition, based on the received signal information and/or stored information. In exemplary embodiments the change may be a physiological change, mental change, emotional change, a physiological response to external or internal stimuli, process or event or an abnormal change that may be detected when the received signal information is not within normal limits or in accordance with one or more predefined medical limits. For example, abnormal conditions, such as hyperglycemia, hyperhidrosis, tachycardia, heart failure, neurological disorder, hemorrhage, and/or other biological, chemical, and/or physiological dysfunctions, such as a sudden onset of paralysis, associated with a subject such as the user or the subject being monitored, may be detected based on the received signal information.

In another embodiment of the present invention, the system comprising processing means is configured to detect subject physiological parameters during any body movement, vibration, rotation of the subject, any motion scenarios or in rest due to absence of relative motion. The processing means is configured to source separating by component analysis a mixture of detected signals and further to recover and extract the desired and preselected component signal(s) from a mixture of signals.

Figure 2:
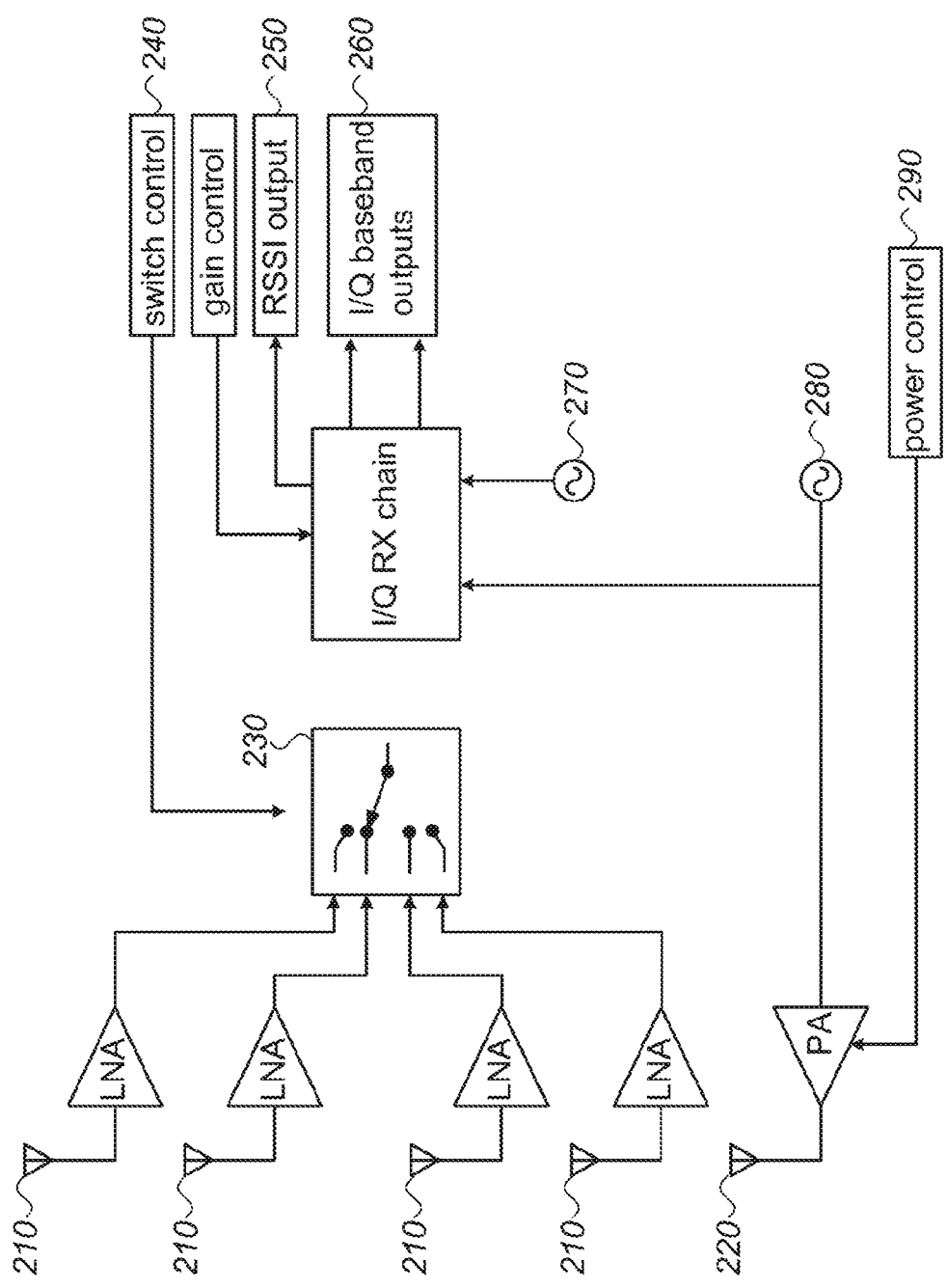
FIG. 2 presents an example of a schema of the Sub-THz and THz radar system according to an exemplary embodiment of the disclosure.
Figure 3:
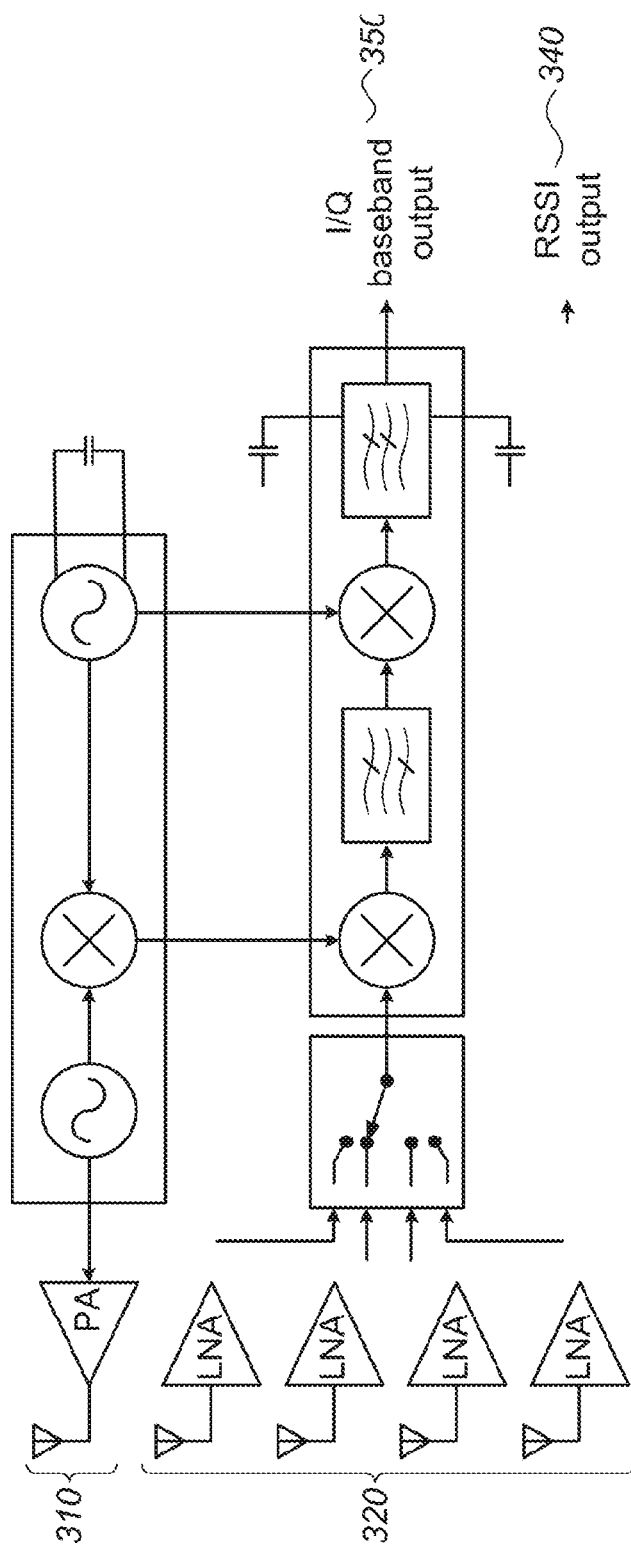
FIG. 3 presents an example of a schema of the Sub-THz and THz radar system according to an exemplary embodiment of the disclosure.

Reference is now made to FIGS. 2 and 3 which presents schemas of the radar system as a single-frequency full duplex which may be continuous wave (CW) or frequency-modulated continuous wave (FMCW) radar system transceiver with integrated antennas and analog intermediate frequency (IF) or baseband output. The system may comprise an MCU for setup, control, A/D conversion cloud-based processing and any data processing means.

The system may further comprise a frequency synthesizer which generates both the Tx output frequency fix and the Rx local frequency fin. The transmit path consists of one or more power amplifier(s) 290 and may have of one or more Tx antenna(s) 220,320. The receiver may have one or more receiver (Rx) antennas 210,310. The receiver may be a heterodyne (i.e. homodyne or superheterodyne). When the receiver is superheterodyne $f_{LO}$ is shifted from $f_{TX}$ by a constant $f_{IF}$. A second downconversion with $f_{IF}$ is used to obtain the baseband signal.

A quadrature IF and baseband structure provides image suppression. Both I and Q baseband signals 260,350 are available on the output.

In other embodiments of the present invention, the system may be configured as a phased array radar system therefore, a computer-controlled array of a plurality of antennas which creates a beam of radio waves that can be electronically steered to point in different directions. Furthermore, the phased array may be configured as a radar of antennas array in a range of about 2×2 to about 16×16 design pattern (e.g. array of 8×8, 4×8, 4×4 or 4×6).

In other embodiments of the present invention, the system may further be configured as a phased array radar such that when simultaneously more than one beam is formed with sufficient angular resolution and further directed towards one or more subjects to be measured, and the beams spot sizes are sufficiently spatially separated. This may further enable to measure and determine subject's physiological parameters such as pulse wave velocity (PWV) derived from information simultaneously collected from the received signals of the adjacent regions on the subject.

In another embodiment of the present invention, the radar system may be characterized by a receiving path comprising four switch selectable Rx antennas 230 to reduce the probability of multipath fading, an external switch control 240, gain control and/or received signal strength indicator (RSSI) output 250,340.

In another embodiment of the present invention, the PWV of a subject could be measured by utilizing the information collected from at least two point to point synchronized radar systems whose beams are directed at spatially separated regions of the subject.

In another embodiment of the present invention, the use of a plurality of transmitter and receiver antennas may be adapted to facilitate the generation of the signals that may show the difference in arrival angles or spatial phases to identify at least one subject from the multiple reflecting signals.

In another embodiment of the present invention, the use of a plurality of transmitter and receiver antennas may be adapted to facilitate the formation of a range, bearing and reflectivity map the measurement environment. This includes the facilitation of sub-THz or THz based image formation.

The receiver may consist of a superheterodyne (dual conversion) with quadrature IF signal path. A crystal oscillator 270 is used to shift the RF oscillator frequency 280 to get the first local signal for the RF downconversion mixer. It further provides the second local signal for the IF downconversion mixer. In order to keep the receive chain in the linear region as much as possible, the gain of both the RF stages (LNAs) and IF stages are digitally selectable. The receiver may also consist of direct heterodyne conversion with or without quadrature demodulation. In this illustration, the mm-wave system may be a system-on-chip (SoC) that operates at the sub-THz and THz wave range.

In other embodiments of the present invention, the radar system may comprise silicon transceivers operating at a range of about 60 to about 500 GHz and more particularly of about 77 GHz to 160 GHz. The on-chip antenna array provides efficient radiation and reception. This system consumes low power and provides enhanced performance for a variety of applications that utilize such information to include range, range rate, and bearing to a target, including coarse and fine scale changes in range and range rate, and target reflection strength.

In other embodiments of the present invention, the system further comprising microprocessor means communicating with the transmitter means and/or the receiver means, for receiving the transmitted signals and processing the reflected sub-THz and THz signal. The microprocessor means configured to analyze the received signals to determine range, range rate, and bearing to a target, including coarse, fine scale changes in range, range rate, and target reflection strength. The microprocessor may further provide vital signs information of the subject detected, such as heartbeat interval, instantaneous heart rate, time averaged heart rate, heart rate variability, respiration interval, time averaged respiration rate, respiration rate variability, and respiration amplitude. The signals may further be processed to suppress the effects random relative motion between the system and the target being observed, allowing for accurate determination of vital sign information in the presence of relative motions.

In another embodiment of the present invention, derived from the physiological parameters or vital signs information, the microprocessor means may further provide a short-term output of data interpretation indicating the subject health status such as fatigue status, sleep status, emotional, mental, physical (i.e. dead or alive) or/and physiological status (i.e. stress, anxiety, physiological crisis and subject comfort level.

In another embodiment of the present invention, the system may further provide a long-term data analysis over time based on a stored system information or/and output in order to detect changes and trends in physiological parameters and bodily functions and for further medical diagnostic.

In another embodiment of the present invention, the system may further export an output associated with the health status selected from the group consisting of an alert, an indication flag, an activation instruction of electronic device, electronic message or any combination thereof. The output may be transmitted to the system user, a physician, user's Electronic Medical Records, a support center, emergency medical services, medical facility or/and autonomous vehicle control center. The alert may be a light source, noise pattern, small and high-frequency oscillation to alert and indicate the user of any change in the measured parameters, electronic message platform. This may further provide an indication of status change, identified increased risk, identified change, trend that requires attention of the user or his physician or any other organization or person that is authorized by the user to be alerted.

In other embodiments of the present invention, the system may further comprise a processing unit providing instructions of a subject classification mechanism for identifying, classifying and/or ranking subject and the received physiological parameter signals according to at least one identification (ID) data stored in the system. The ID data is selected from the group consisting of subject's age, gender, race, mental condition, physiological condition, health condition, medical history, subject assessment data, size, height, weight, shape, stored health profile and a combination thereof.

In other embodiments of the present invention, the processing may further comprise instructions to compare baseline characteristics of a subject, between a plurality of subjects or between predefined groups (i.e. according to rang of age, health condition etc.), in the same space or environment. Therefore, the system may provide an output in relation to the difference or change in subject's characteristic or status within a predefined space.

The processing unit may further be synchronized with data selected from the group consisting of physiological data, physical data, medical centers, health maintenance organization, medical records, medical history of the subject and a combination thereof.

In other embodiments of the present invention, the processing unit may further communicate with a manned control center which may further transmit instructions to the system for controlling subject's environment or vehicle systems. The processing unit is further configured to collect and/or store the received signal information. The information recorded can be transmitted to any display device or electronic device to allow the subject, system user or/and caregivers to observe the information and provide feedback for further progress, diagnostic and treatment.

In accordance of the present invention, the processing unit may further generate instructions transferred to at least one user via an electronic device selected from the group consisting of an electronic control unit (ECU), a server, a mobile device such as a smartphone, handheld device, a wearable device and any combination thereof.

In other embodiments of the present invention, the system may further comprise additional sensors communicating with the processing means, therefore generating sensor fusion by integrating sensory data or data derived from disparate sources such that resulting in a more accurate and complete information and further increasing confidence level or the processing unit for data interpretation and decision making. The sensor fusion may be a direct fusion, indirect fusion or a combination of the output of the direct and indirect. The sensory data may be derived from a variety of sensor types, a camera or any thermographic camera (i.e. infrared camera, thermal imaging camera or infrared thermography). Therefore, the system may be based on sensory data fusion to identify and differentiate between several subjects in a predefined space and to provide an electromagnetic image of at least one subject.

In other embodiments of the present invention, the radar system of the present invention may be a CMOS-based system, SiGe based system or based upon other semiconductor technologies. The CMOS-based system is configured to receive, transmit and analyze the detected beam by an electronic circuit and identifying at least one physiological parameter of the subject and related change.

In other embodiments of the present invention, the system may be located at any desired location and simultaneously spatially resolve, distinguish, and determine the physiological parameters arising from multiple subjects by way of utilizing differing range, angular azimuthal, and/or angular elevation information to each uniquely distinguished subject detected. Furthermore, this may facilitate the identification of a plurality of subjects based on the differences of differing range, angular azimuthal, and/or angular elevation information to each uniquely distinguished subject detected.

In other embodiments of the present invention, the system provides non-ionizing radiation and is safe to use for a variety of applications. Therefore, the system may be employed for the automotive industry, testing methods, healthcare applications and facilities, elderly or/and baby monitoring applications and security applications. Additional applications may include biometric measurements, speech recognition, non-destructive testing of covered objects.

In another embodiment of the present invention, microvibration in the present disclosure may include nano-vibration i.e. vibration processes on both nanometer and micrometer scale. In other embodiments of the present invention, the system may further be configured to detect the dielectric properties of various mammalian tissue and biological fluids for the frequency range from 1 Hz to 10 GHz by measuring the received reflected signal and computing the reflectivity of the tissue being observed.

In other embodiments of the present invention, the system may further comprise a signal to noise ratio (SNR) or an information-based content means for reducing and/or removing noise from predefined signal selected from the group consisting of ambient noises, voices, sounds, motions and any combination thereof. Thereby, enabling to obtain a low noise signal.

In other embodiments of the present invention, the system may be a miniaturized system within a vehicle, subject home or/and medical institute/facility, which further located, placed, build in, mounted, coupled, attached, embedded or integrated, in a variety of devices, articles, surfaces, any housing, location or portion of any object, desired environment or electronic circuits or devices. For example, within the vehicle such as, car seat, door, in-car entertainment (ICE) system, the control system of the vehicle, seat belt, dashboard, vehicle hood, internal lighting aperture, center console or any other region, platform, circuitry or interface within the vehicle. For example, within the subject's home or medical facility such as any furniture, assembly, object, article, region, platform, electronic device, circuitry or interface located in the house or medical facility.

In another embodiment of the present invention, the system may further comprise a communication network which includes a wired medium or wireless medium through which the use or an electronic device may communicate with one or more servers and external communication mediums associated with one or more of medical services providers. Examples of the communication network may include, but are not limited to, an Internet, a cloud network, a Local Area Network (LAN), a telephone line (POTS), a Metropolitan Area Network (MAN), a Wireless Local Area Network (WLAN), and/or a cellular network, such as a long-term evolution (LTE) 3G and/or 4G network. Various devices in the network environment may be operable to connect to the communication network, in accordance with various wireless communication protocols. Examples of such wireless communication protocols, communication standards, and technologies may include, but are not limited to, Transmission Control Protocol and Internet Protocol (TCP/IP), User Datagram Protocol (UDP), Hypertext Transfer Protocol (HTTP), Long-term Evolution (LTE), File Transfer Protocol (FTP), Enhanced Data GSM Environment (EDGE), voice over Internet Protocol (VoIP), a protocol for email, instant messaging, and/or Short Message Service (SMS), and/or cellular communication protocols.

In another embodiment of the present invention, the communication network may further correspond to a vehicle-to-vehicle communication. Therefore, the system may be placed in a first vehicle for detecting subject's physiological parameters associated with the first subject and further communicates with a second vehicle control system.

The system processor may further provide a short-term output of physiological parameters data interpretation indicating the subject health status such as fatigue status, sleep status, emotional, mental, physical) or/and physiological status (i.e. stress, anxiety, physiological crisis and subject comfort level and further communicate with a second vehicle providing activation instructions derived from subject's health status.

For example, if subject's health status indication in a vehicle is fatigue, the system may report 'fatigue' and vehicle control system may deactivate "autopilot" operation, with or without a warning to the subject or alternatively it will not allow engagement of the "autopilot" operation due to driver fatigue.

Another exemplary embodiment may be if subject's health status indication in a vehicle is in a sleeping state (i.e. falling asleep or deep sleep) system may report 'sleep' and vehicle control system may deactivate hand-back control operation. Alternatively, the system may provide instructions to deactivate the vehicle in a safe manner and/or transmit an awake alert to the subject via vehicle control system (i.e. light, audio, air condition or any haptic feedback). Furthermore, if the vehicle control system reports malfunction and the subject is 'sleeping' the control system may direct the vehicle to stop at the side of the road instead of handing back control to a non-functioning subject.

Another exemplary embodiment may be when subject's health status indication is in a medical emergency state, the system report 'emergency' and may communicate with emergency services, deactivate the vehicle in a safe manner and/or instruct the vehicle control system to direct the vehicle to a preselected medical facility or to stop at the side of the road and await emergency services.

Another exemplary embodiment may be if a subject's health status indication in an autonomous vehicle, is in a sleeping state (i.e. falling asleep or deep sleep) system reports 'safe sleep' and vehicle control system enables vehicle comfort status (i.e. reduce noise in cockpit, windows transparency, audio volume etc.).

In another embodiment of the present invention, the communication network may include, but is not limited to a dedicated short-range communication (DSRC) network, Bluetooth, Wi-Fi, a vehicular ad-hoc network (VANET), Intelligent vehicular ad-hoc network (InVANET), Internet-based mobile ad-hoc networks (IMANET), a mobile ad-hoc network (MANET), a wireless sensor network (WSN), a wireless mesh network (WMN), a Wireless Local Area Network (WLAN), and/or a cellular network, such as a long-term evolution (LTE) 3G and/or 4G network.

Figure 4:
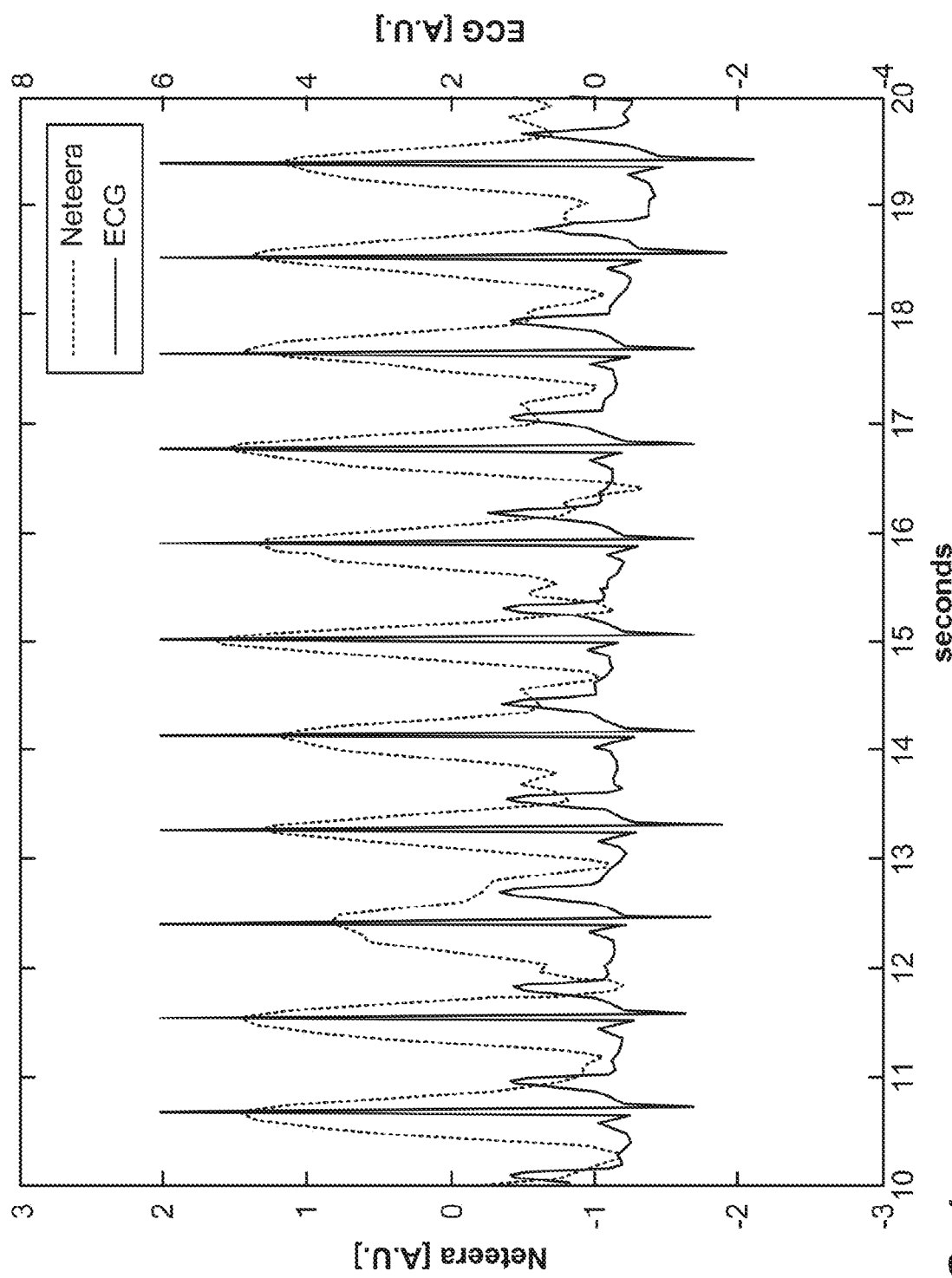
FIG. 4 presents a graph of BCG and ECG data sets, simultaneously measured according to an exemplary embodiment of the disclosure.

Reference is now made to FIG. 4 illustrating a graph of Ballistic Cardiogram (BCG) and Electrocardiogram (ECG)

data sets, simultaneously measured using the THz system of the present invention and regular ECG technologies.

In some embodiments of the disclosure, the radar system includes a radio platform, a radar antenna, a signal processing unit, transmission means, processing means, system media, and a system manager.

In some embodiments of the disclosure, the system is configured to monitor the heartbeat and/or respiration rate of a human in a remote and real-time manner. The performance of the system can be demonstrated by comparing the simultaneously measured vital signals by the system of the present invention, the Ballistic Cardiogram (BCG), and a real ECG.

Figure 5:
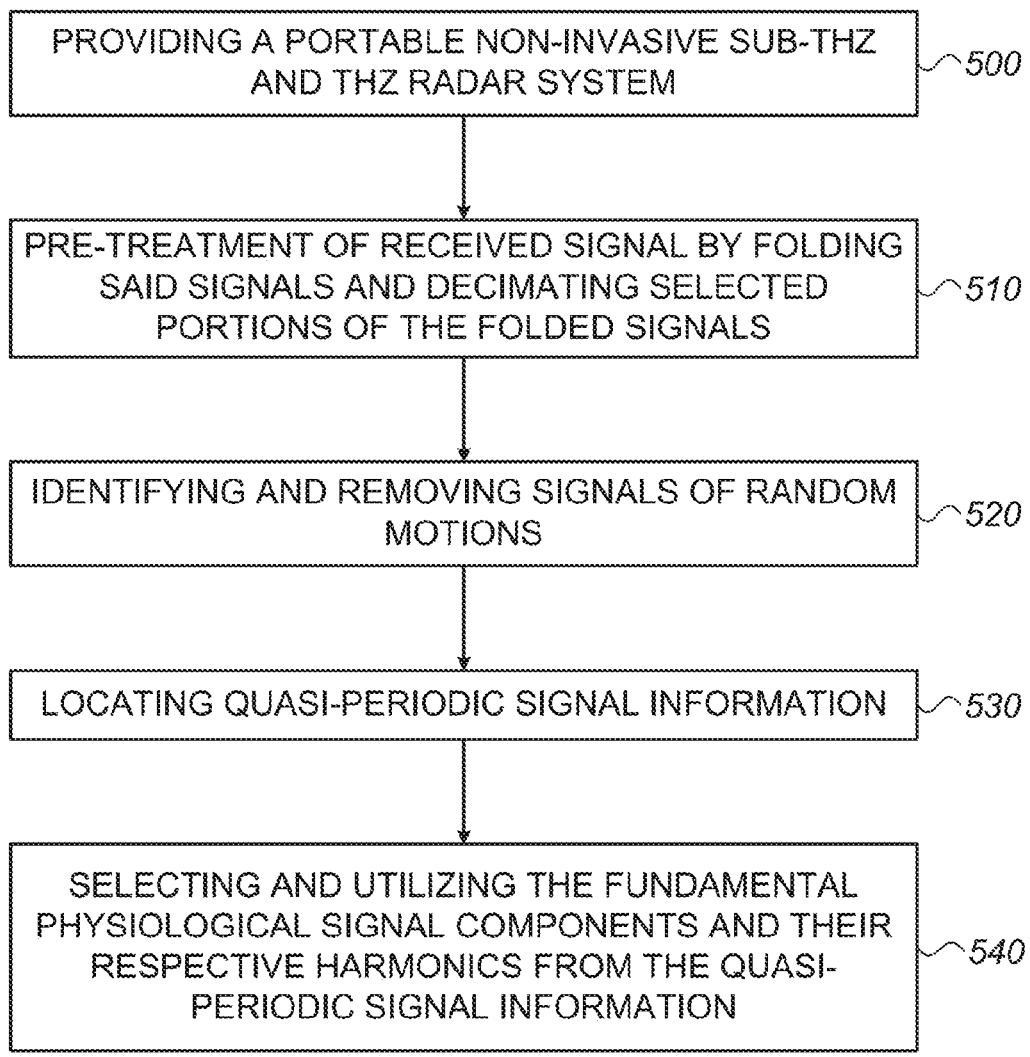
FIG. 5 presents a flowchart of a method of detecting physiological parameters of a subject according to an exemplary embodiment of the disclosure.

Reference is now made to FIG. 5 which presents a flowchart of a method of remotely detecting at least one physiological parameter of at least one subject in a distance of space, comprising steps of: providing a portable non-invasive sub-THz and THz radar system for remotely detecting physiological parameters of a subject (500), comprising: one or more transmission means for transmitting sub-THz and THz signals to a subject predefined tissue, one or more reception means for receiving a THz signal of the subject, the THz signals being a reflection of the THz signal from subject tissue thereby, receiving at least one physiological parameter change and a microprocessor communicating with transmission means and/or reception means for receiving the transmitted signals and processing the reflected THz signal.

The method further comprising the steps of processing received signals by analyzing the received signals. Therefore, the extracted signal may be processed, and analyzed to determine subject physiological parameters such as the exact respiration rate and/or heart rate of the subject.

In another embodiment of the present invention, the received signals may be pre-treated (510), processed, calculated, analyzed and/or interpreted. The step of pre-treatment (510) of the received signal includes filtering i.e. folding or mirroring the signals and decimating selected portions of the folded signals and removing folded segments. This further enables appropriate bandpass filtering and removing the folded portions of data (520).

The method further comprising motion noise suppression by locating quasi-periodic signal information; this step can suppress the effects of random noise relative to the quasi-periodic vital sign data (530).

The method further comprising component selection facilitated and/or manipulated by way of an intelligent decision tree to retain relevant components that are generated from the previous step and allows for determining the fundamental vital sign components based upon the remaining spectral content and their harmonic behavior and groupings (540).

The method may further comprise the step of selecting and utilizing the fundamental physiological signal components and their respective harmonics from the remaining sub-component signals.

The method further comprising physiological parameters computation and tracking. The tracking may be accomplished by using a particle filter tracker or any modification of such and even limited to 1 dimension.

Figure 6:
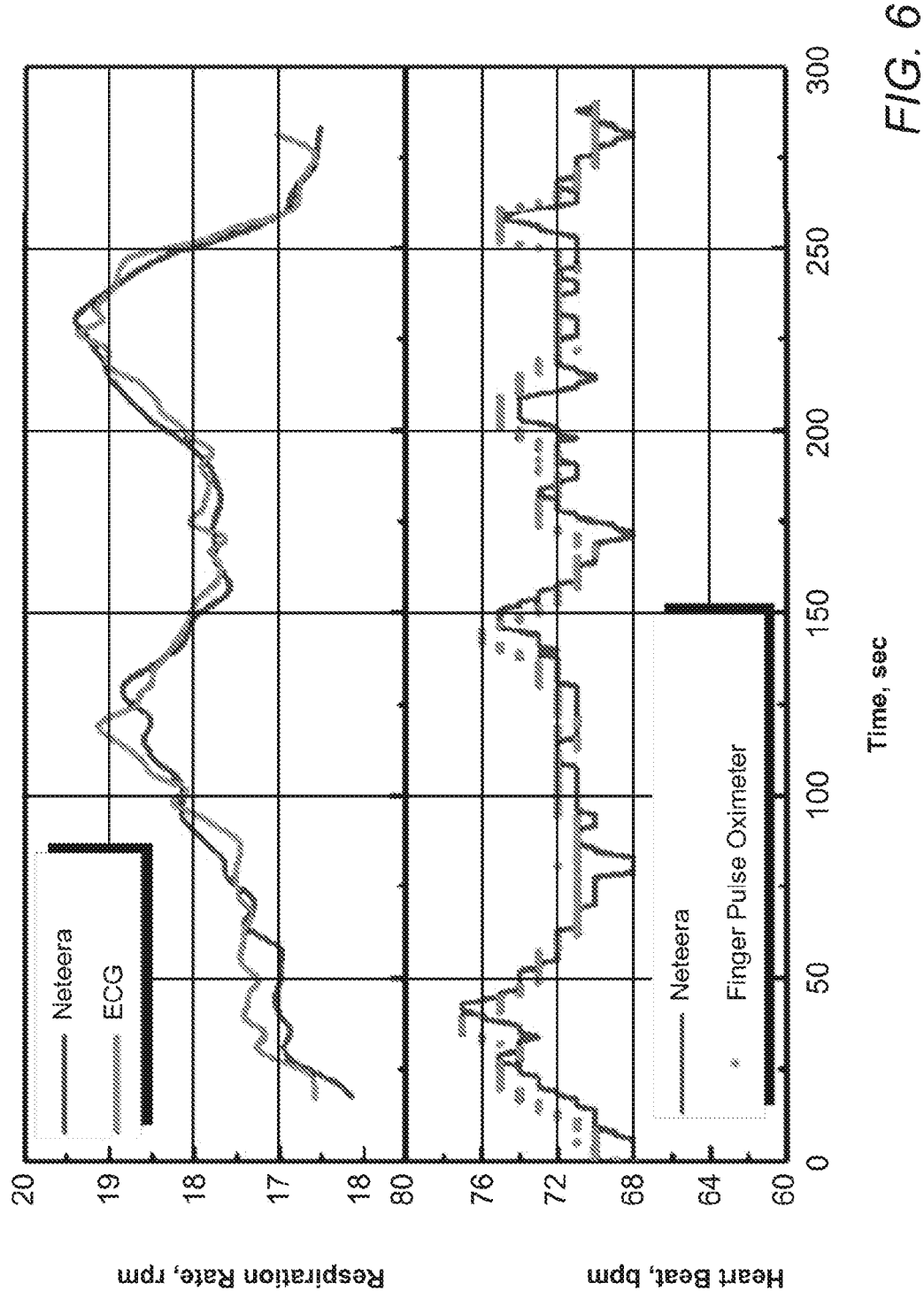
FIG. 6 illustrates a graph of the comparison of heartbeat and respiration rate data sets tracks according to an exemplary embodiment of the disclosure.

Reference is now made to FIG. 6 which presents a time series graph of a comparison of heart rate and respiration rate data sets detected by the THz system of the present invention and ECG or Finger Pulse Oximeter sensors (FDA certified).

As shown in FIG. 6, the achieved results, where the upper graph represents the respiration rate results and bottom graph the heart rate results. The tolerance analysis of the present invention system and ECG or Finger Pulse Oximeter techniques (FDA certified) shows a difference of no more than 5%. That demonstrates the ability of the system of the present invention to accurately monitor vital signs of the human body.

Figure 7:
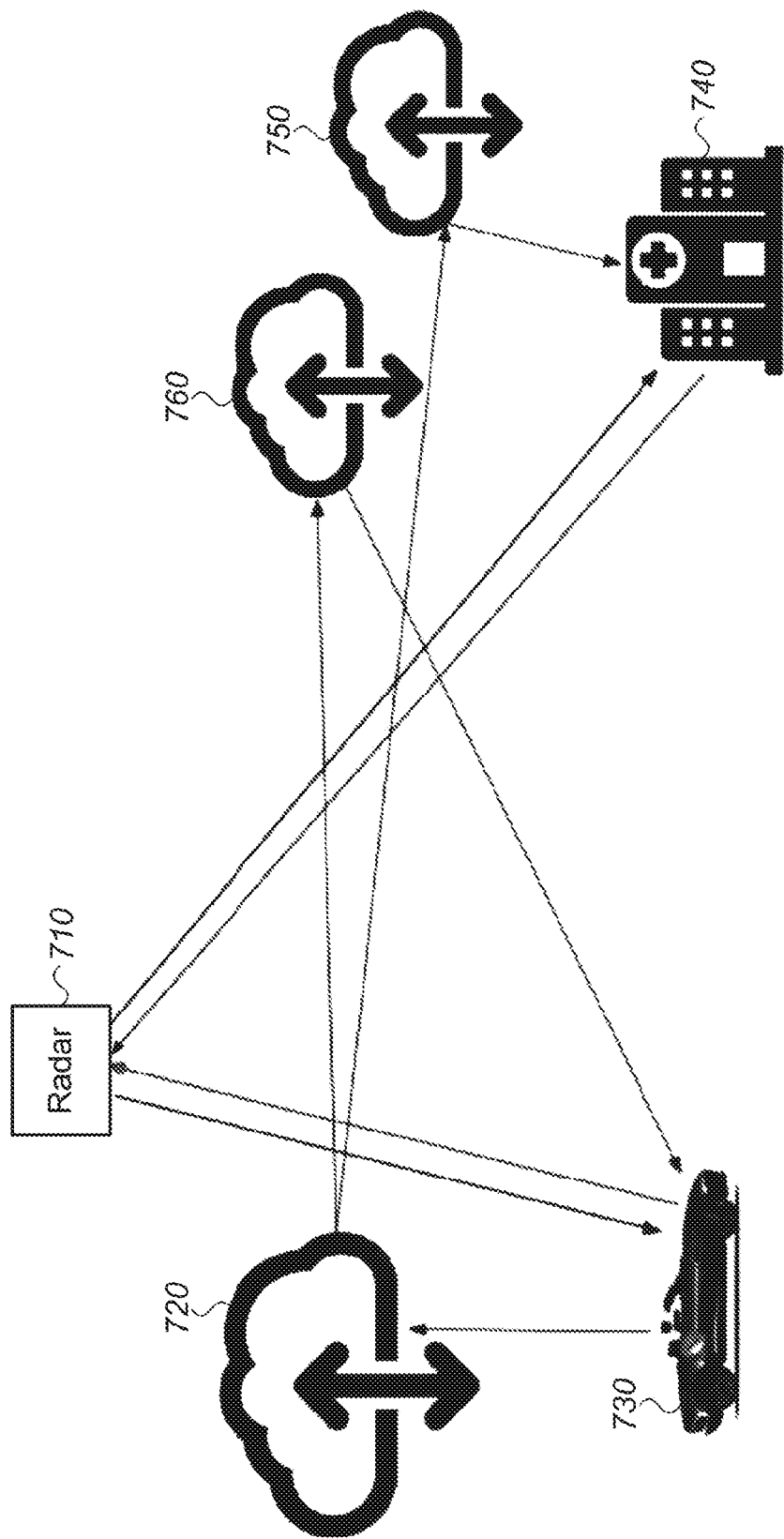
FIG. 7 presents a schematic view of the cloud-based system communication according to an exemplary embodiment of the disclosure.

Reference is now made to FIG. 7 illustrating the cloud-based system of the present invention. As illustrated the cloud-based system 720 may communicate with a plurality of sources such as the present invention THz radar system 710, a medical center/healthcare center 740, another OEM vehicle 730, cloud-based control center 750, OEM cloud-based system/center 760 or any other data source system and facility.

In other embodiments, the system may further comprise a server which communicates with any electronic circuit or device associated with a user, medical care center, predetermined users, caregiver, emergency services and/or a service control unit. The communication may be via a wireless communication means. The receiving information is stored in the processing unit or/and in the cloud-based system.

Figure 8:
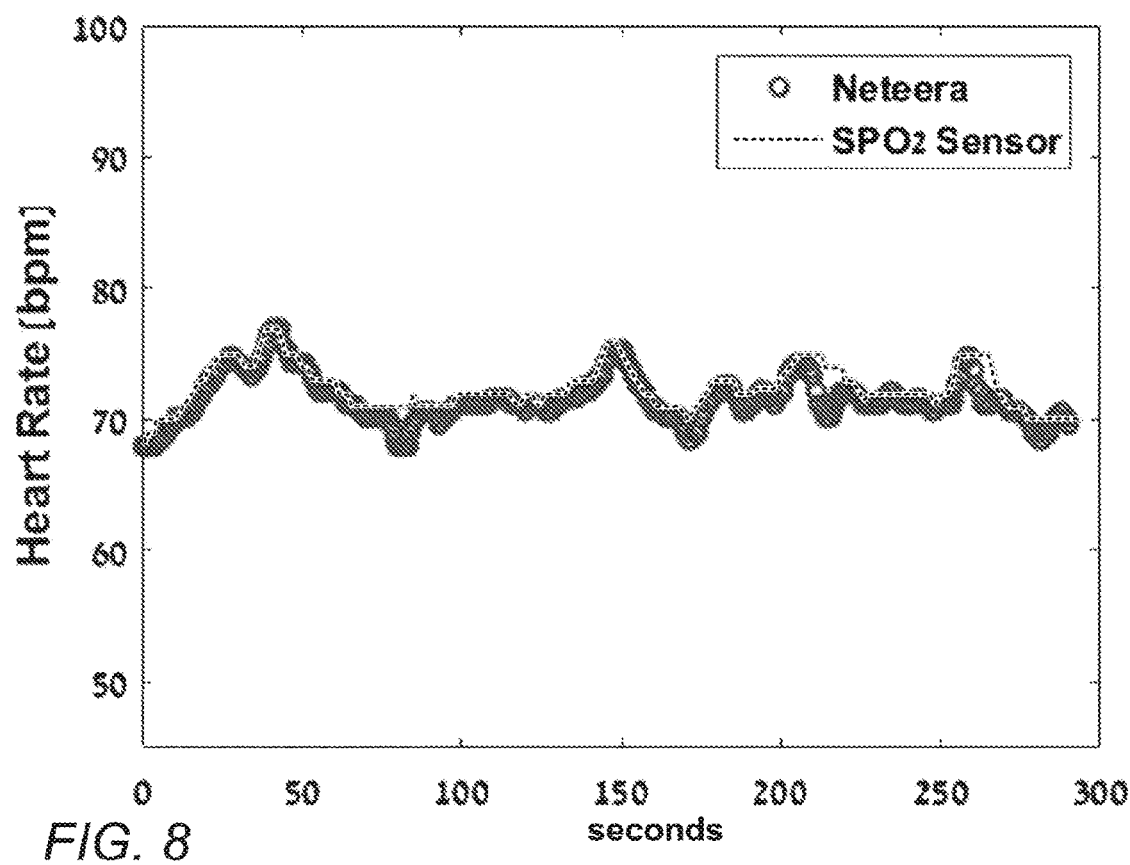
FIG. 8 presents a graph of subject measured heart rate vs. time in a vehicle according to an exemplary embodiment of the disclosure.

Reference is now made to FIG. 8 which presents a graph of the subject's measured heart rate (bpm) vs. time (secs). The graph further presents STFT computed HR conducted in a vehicle and further compared $SPO_2$ ground truth HR data.

As can be observed the heart rate measurements using the present invention radar system provide similar results as $SPO_2$ sensor measurements (FDA certified).

Figure 9:
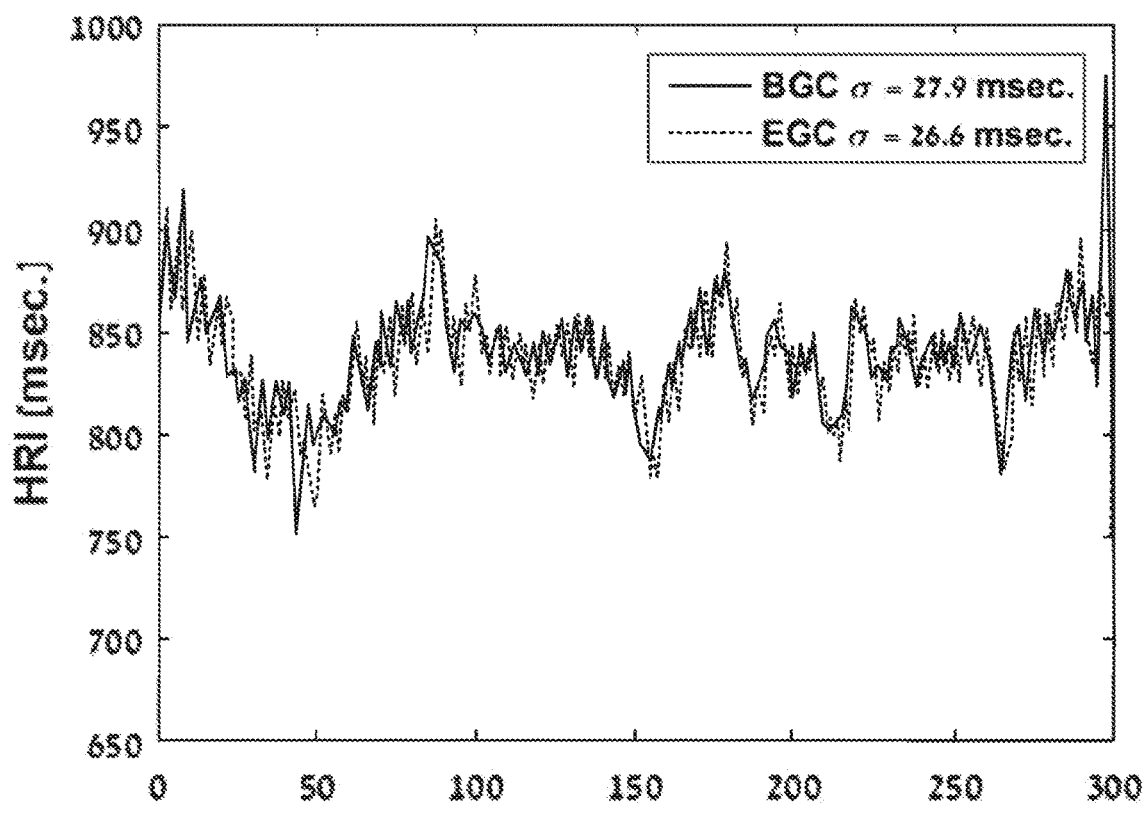
FIG. 9 presents a graph of subject measured heart rate vs. time in a vehicle according to an exemplary embodiment of the disclosure.

Reference is now made to FIG. 9 which presents a graph of the subject's measured HRI (msec.) vs. time (secs). The computed HRV from the time domain BCG based HRI data using SDNN is 27.9 mesc. and further compared to a common ECG sensor having a computed SDNN HRV value of 26.6 mesc which is less than 5% difference between measurement systems.

Figure 10:
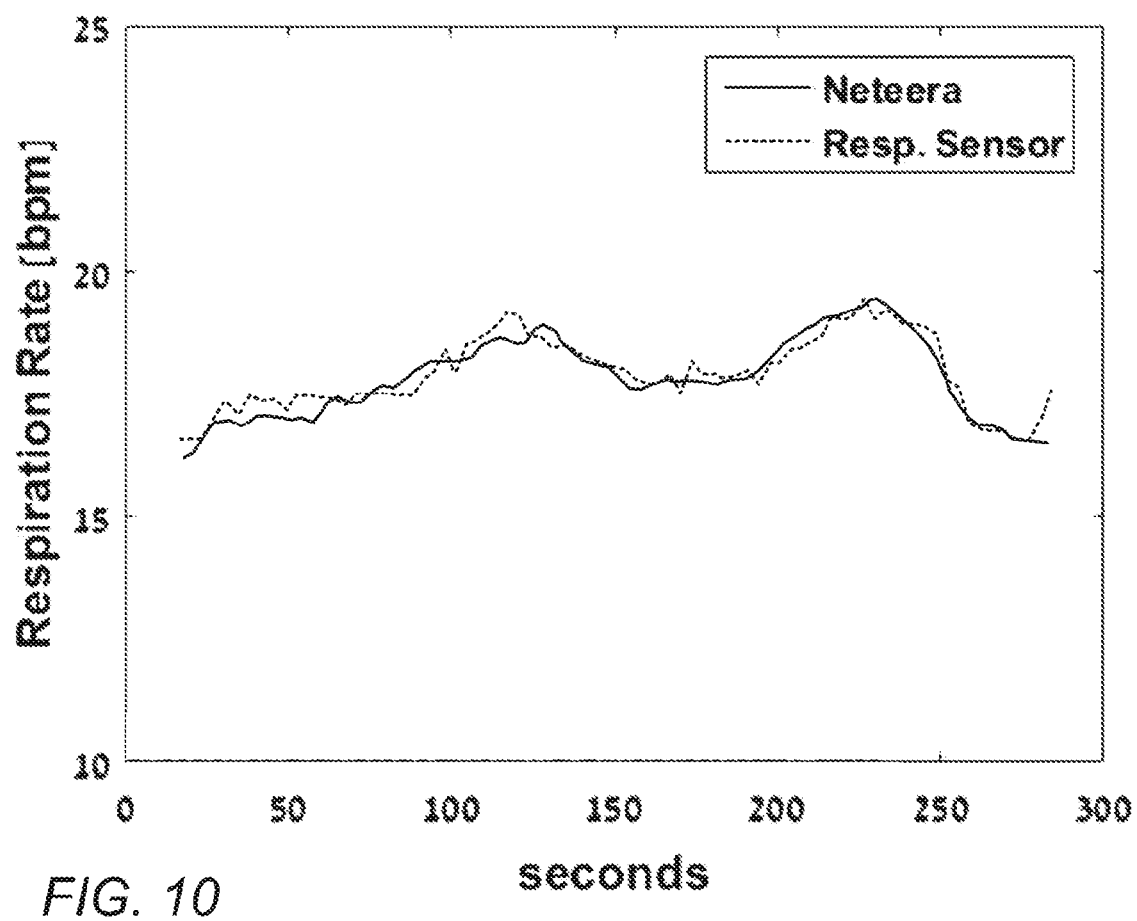
FIG. 10 presents a graph of subject measured respiration rate vs. time in a vehicle according to an exemplary embodiment of the disclosure.

Reference is now made to FIG. 10 which presents subject measured respiration rate (bpm) vs. time (secs). The respiration rate data was conducted in a vehicle and processed from the system of the present invention and compared to a common respiration sensor.

Figure 11:
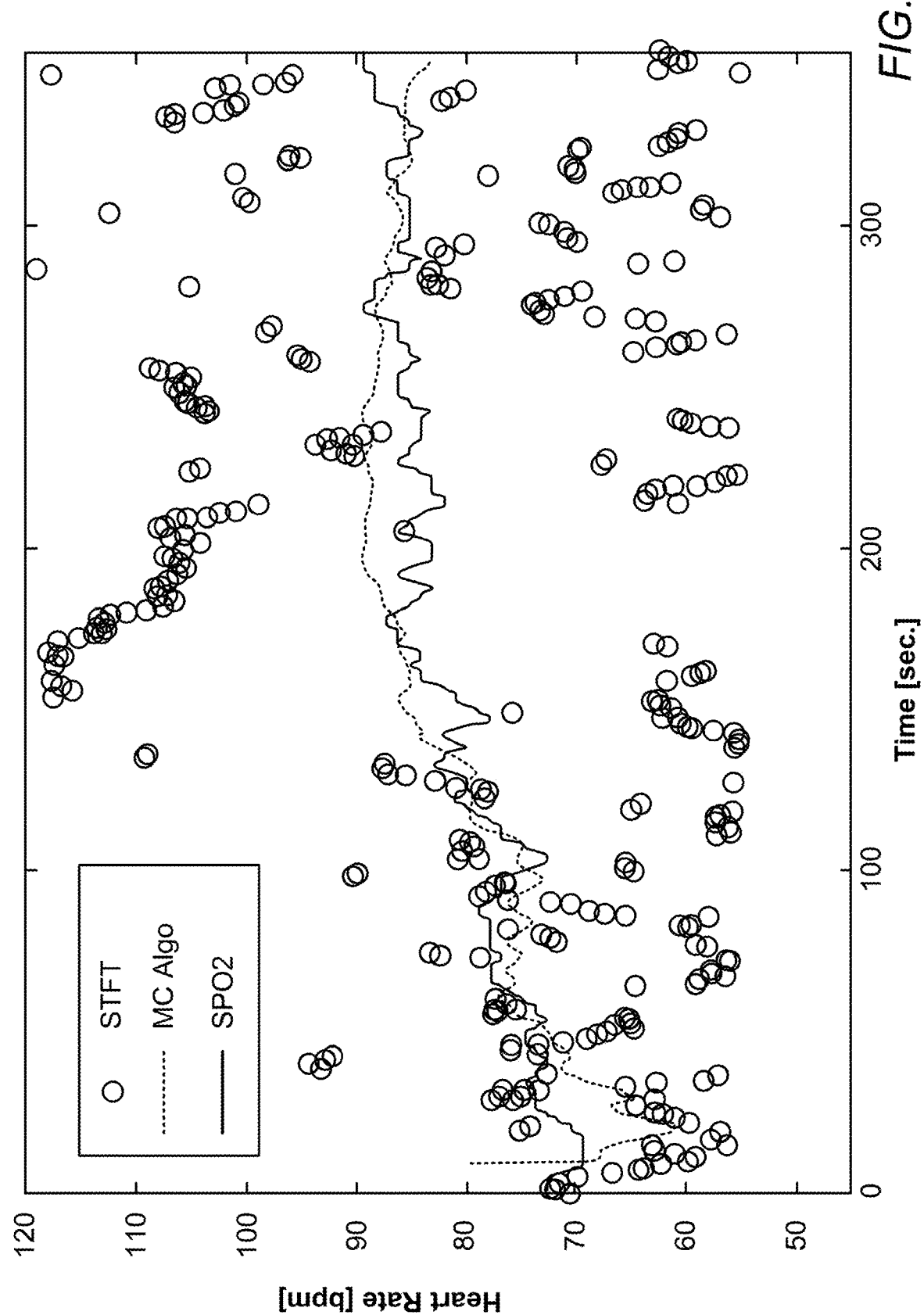
FIG. 11 presents a graph of subject measured heart rate vs. time in a vehicle according to an exemplary embodiment of the disclosure.

Reference is now made to FIG. 11 which presents a graph of heart rate (bpm) vs. time (mins) for a measurement conducted in a vehicle. The data was detected and processed using the system of the present invention. The measurements were conducted using the system of the present invention mounted on the back of car seat and where the test subject slowly increased the random body motions and simultaneously his HR was raised. Furthermore, HR predictions for both standard processing (STFT) as well as for the motion compensation algorithm (MC Algo) and compared with ground truth sensor data ($SPO_2$, FDA certified).

Figure 12:
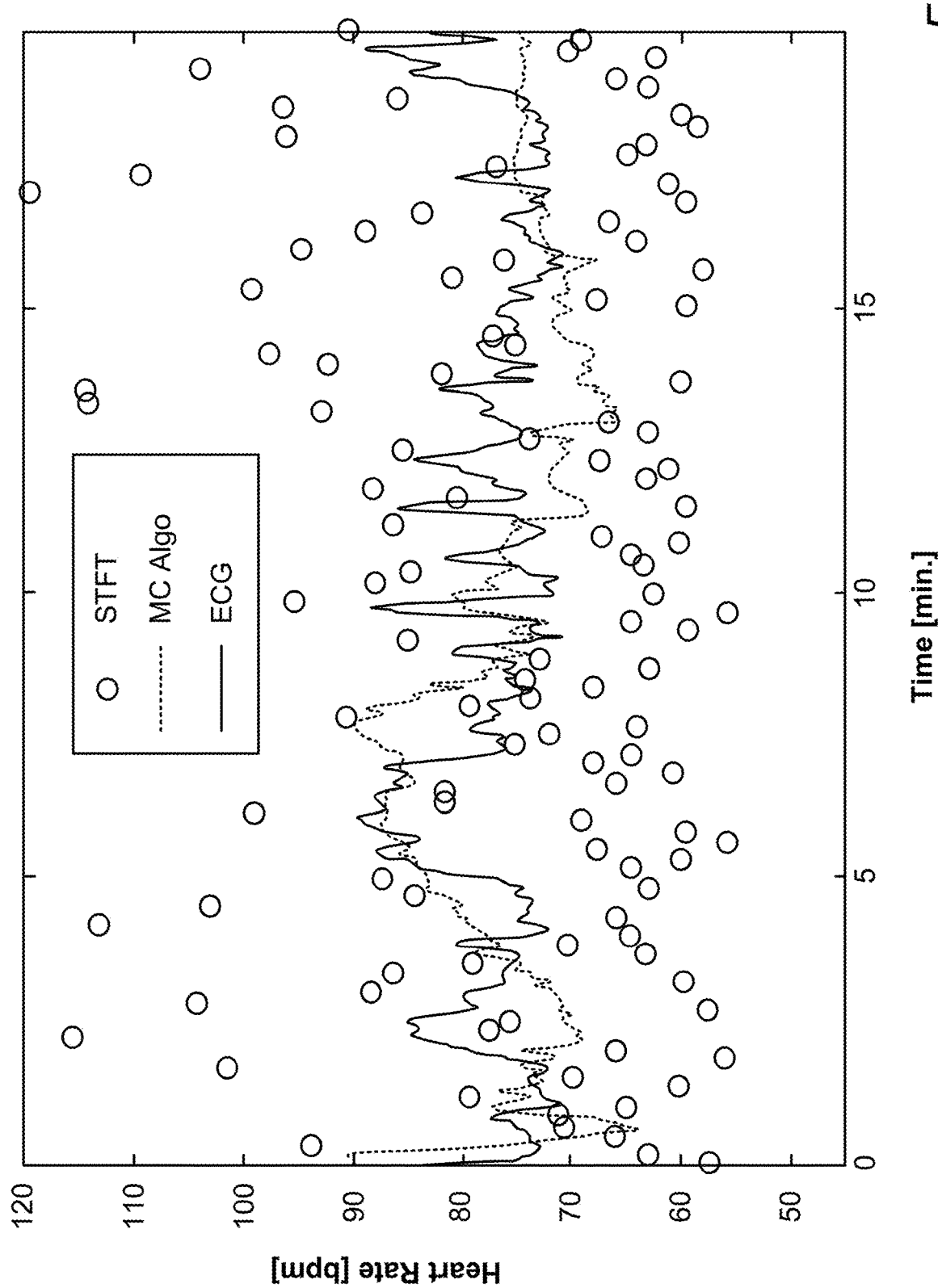
FIG. 12 presents a graph of subject measured heart rate vs. time in a vehicle according to an exemplary embodiment of the disclosure.

Reference is now made to FIG. 12 which presents a graph of heart rate (bpm) vs. time (mins) measurements in a vehicle. The data was detected and processed using the system of the present invention.

The measurements were conducted as a road test monitoring of driver's vital signs during highway driving. HR results are shown for both standard processing (STFT) of the present invention system as well as for the motion compensation algorithm (MC Algo) and compared with the HR as determined by a common ECG.

Figure 13:
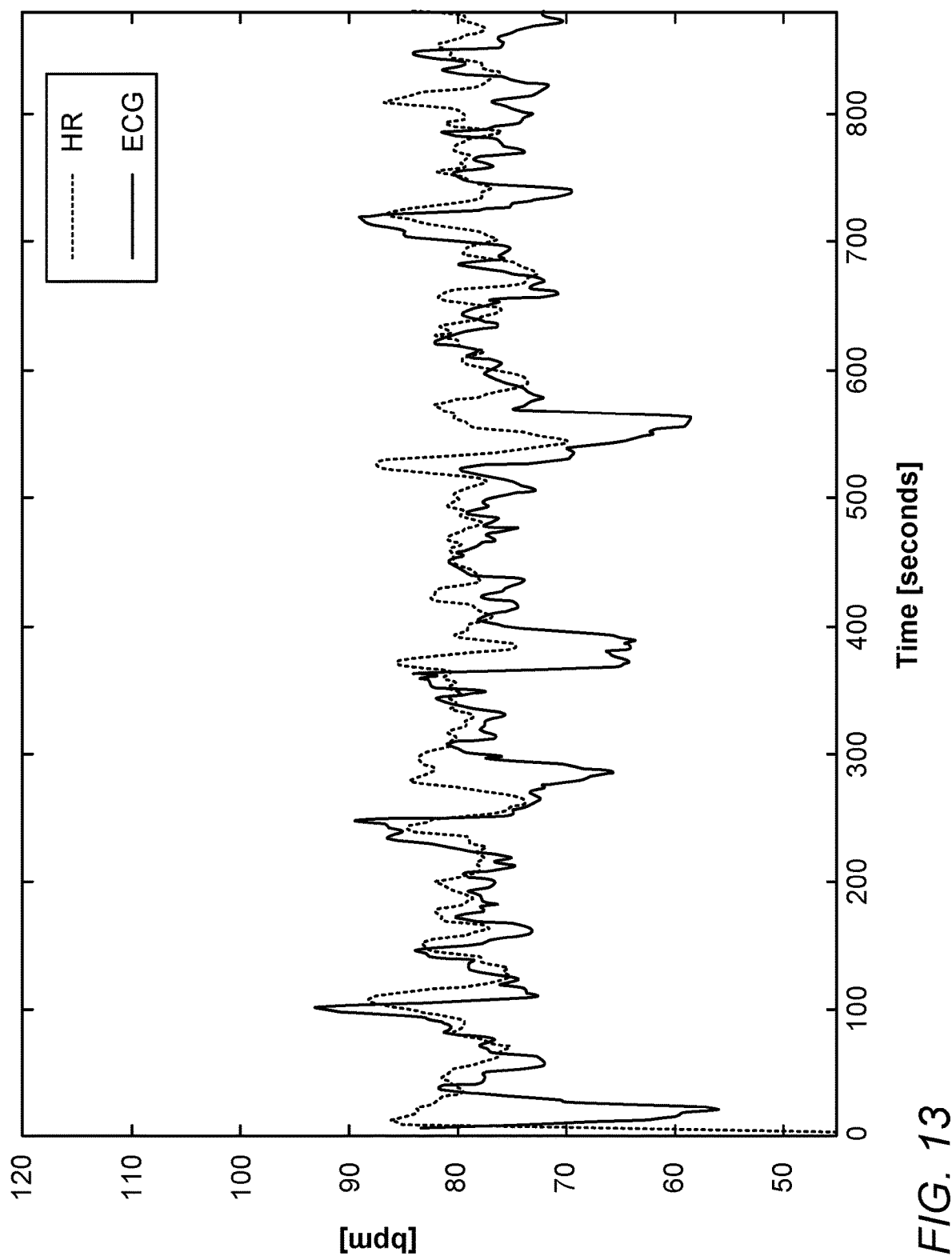
FIG. 13 presents a graph of subject measured heart rate vs. time in a vehicle according to an exemplary embodiment of the disclosure.

Reference is now made to FIG. 13 which presents a graph of heart rate (bpm) vs. time (secs) from an in-vehicle installation. The data was detected and processed using the system of the present invention. The heart rate results were further compared with a common ECG, illustrating similar heart rate detection results.

Figure 14:
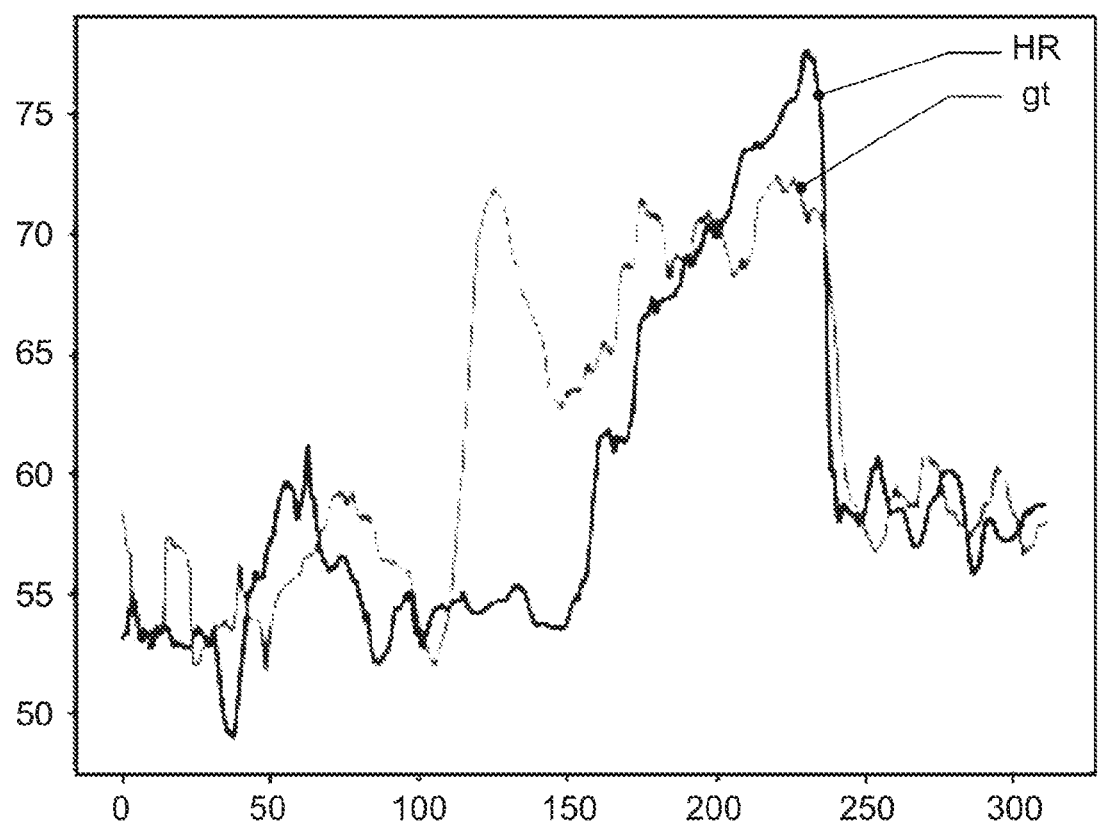
FIG. 14 presents a graph of subject measured heart rate vs. time in a vehicle according to an exemplary embodiment of the disclosure.

Reference is now made to FIG. 14 which presents a graph of measured heart rate (bpm) vs. time (secs) of a subject engaging in nominal motions while otherwise positioned in a car seat located inside a laboratory setting. The motion was comprised of mild heading turning, hand and arm motion such that standard processing failed to accurately predict the subject's HR.

The data was detected and processed using the system of the present invention.

The subject being tested was instructed as follows:
(a) 0-120 seconds the subject is not speaking
(b) 120-240 seconds the subject is speaking which causes additional random body motions and an increase in HR.
(c) 240 seconds until the end the subject is no longer speaking, and the HR returns to normal.

Those results further illustrate that the undesired signal data were further separated or isolated by the system from the extracted signal thus, and successfully tracked the desired heart rate output signal data for the duration of the measurement.

The invention claimed is:

1. A method of remotely detecting at least one physiological parameter of at least one subject, the method comprising:
providing a portable non-invasive sub-THz and THz radar system for remotely detecting physiological parameters of a subject, comprising:
one or more transmitters, configured to transmit a transmitted signal to tissue of the subject, at a frequency range of 0.03 to 3 THz;
one or more receivers, configured to receive a reflection of the transmitted signal from said tissue, as a reflected signal; and
a microprocessor configured to communicate with at least one of the transmitter and the receiver, and configured to receive and process the reflected signal; and
using the microprocessor:
pretreatment and folding said reflected signal;
filtering and decimating selected portions of the folded signal, and removing folded segments of the folded signal;
decomposing the decimated signal into sub-component signals;
identifying and removing sub-component signals due to random motions of the subject;
locating quasi-periodic signal components within the remaining sub-component signals; and
selecting and utilizing fundamental physiological signal components and respective harmonics from the remaining sub-component signals to determine at least one physiological parameter of said subject, based upon remaining spectral content and harmonic behavior and groupings thereof.

2. The method according to claim 1, further comprising generating one or more physiological parameter profiles for the subject, based upon the at least one determined physiological parameter, the one or more physiological parameter profiles being selected from the group consisting of: average heart rate vs. time, heartbeat to heartbeat interval, variation in average heart rate, variation in heartbeat interval, temporal change in heart rate variations, spectral change in heart rate variations, respiration intervals, variations in respiration rates, and respiration amplitude.

3. The method according to claim 1, further comprising associating data relating to the at least one determined physiological parameter with a cloud-based system.

4. The method according to claim 1, further comprising:
(a) storing physiological parameter signal information;
(b) interpreting real time received signals compared to stored signal information;
(c) indicating a subject health status selected from the group consisting of: fatigue, sleep, stress, anxiety, physiological crisis, comfort level, and a combination thereof; and
(d) exporting an output selected from the group consisting of: an alert, an electronic message, a flag, an activation instruction of an electronic circuit associated with the health status, and an activation instruction of a device associated with the health status.

5. The method according to claim 1, wherein determining at least one physiological parameter of said subject comprises determining at least one physiological parameter of said subject selected from the group consisting of: heart rate, heart rate interval, heart rate variability, respiratory rate, respiratory rate variability, respiration amplitude, respiration amplitude variability, blood pressure, body temperature, body fluids, vocal cord, eye movement, body movement, motion status, stroke volume, and a combination thereof.

6. The method according to claim 1, further comprising identifying and ranking the at least one determined physiological parameter according to at least one criterion selected from the group consisting of: the subject's age, the subject's gender, the subject's race, the subject's physiological condition, the subject's mental condition, the subject's health condition, the subject's medical health history, and a combination thereof.

7. The method according to claim 1, further comprising simultaneously monitoring one or more additional subjects in a predefined location, using the portable non-invasive sub-THz and THz radar system.

8. The method according to claim 1, further comprising providing sensory data fusion via at least one sensor.

9. A portable non-invasive sub-THz and THz (THz) radar system for remotely detecting physiological parameters of a subject comprising:
one or more transmitters, configured to transmit a transmitted signal to tissue of the subject, at a frequency range of 0.03 to 3 THz;
one or more receivers, configured to receive a reflection of the transmitted signal from said tissue, as a reflected signal; and
a microprocessor configured to communicate with at least one of the transmitter and the receiver, and configured to receive and process the reflected signal, by:
pretreatment and folding said reflected signal;
filtering and decimating selected portions of the folded signal, and removing folded segments of the folded signal,
decomposing the decimated signal into sub-component signals;
identifying and removing sub-component signals due to random motions of the subject;
locating quasi-periodic signal components within the remaining sub-component signals; and
selecting and utilizing fundamental physiological signal components and respective harmonics from the remaining sub-component signals to determine at least one physiological parameter of said subject, based upon remaining spectral components and harmonic behavior and groupings thereof.

10. The system according to claim 9, wherein the system is configured to be housed within a housing selected from the group consisting of: a smartwatch, a microphone, a helmet, headphones, a head-mounted display, a clothing article, a garment, a bracelet, a wrist device, a necklace, a finger ring, glasses, goggles, a patch, and an electronic device.

11. The system according to claim 9, further comprising at least one sensor for providing sensory data fusion.

12. The system according to claim 9, wherein the radar system is configured to be activated in real time by user demand, system offline/online activation or predefined instructions.

13. The system according to claim 9, wherein the microprocessor is configured to isolate un-predefined motion streams of signal data into fundamental components to thereby extract a signal that is indicative of the physiological parameter.

14. The system according to claim 9, wherein said microprocessor is configured to associate data relating to the at least one determined physiological parameter with a cloud-based system.

15. The system according to claim 9, wherein said microprocessor is configured to provide a profile pattern of the subject, based upon the determined physiological parameter, the profile pattern selected from the group consisting of:

a respiratory profile pattern, and a heart rate profile pattern.

16. The system according to claim 9, wherein the microprocessor is configured to determine at least one physiological parameter of said subject selected from the group consisting of: heart rate, heart rate interval, heart rate variability, respiratory rate, respiratory rate variability, respiration amplitude, respiration amplitude variability, blood pressure, body temperature, body fluids, vocal cord, eye movement, body movement motion status, stroke volume, and a combination thereof.

17. The system according to claim 9, wherein the microprocessor is further configured to identify and rank the at least one determined physiological parameter according to at least one criterion selected from the group consisting of: the subject's age, the subject's gender, the subject's race, the subject's physiological condition, the subject's mental condition, the subject's health condition, the subject's medical health history, and a combination thereof.

18. The system according to claim 9, wherein the radar system is configured to simultaneously monitor one or more additional subjects in a predefined location.

19. The system according to claim 9, wherein the microprocessor is configured to generate an indication regarding the subject's health status selected from the group consisting of: fatigue, sleep, stress, anxiety, physiological crisis, comfort level, and a combination thereof.

* * * * *